US011779315B2

(12) United States Patent
Nelson et al.

(10) Patent No.: US 11,779,315 B2
(45) Date of Patent: Oct. 10, 2023

(54) SELF-CONTAINED SAMPLING DEVICE FOR PROCESSING WHOLE BLOOD

(71) Applicant: Tetracore, Inc., Rockville, MD (US)

(72) Inventors: William M. Nelson, Rockville, MD (US); David R. Almassian, Gaithersburg, MD (US); Tracy Calvin Fecteau, Ellicott City, MD (US); Colin Kuserk, Derwood, MD (US)

(73) Assignee: Tetracore, Inc., Rockville, MD (US)

( * ) Notice: Subject to any disclaimer, the term of this patent is extended or adjusted under 35 U.S.C. 154(b) by 131 days.

(21) Appl. No.: 15/654,916

(22) Filed: Jul. 20, 2017

(65) Prior Publication Data

US 2018/0021026 A1 Jan. 25, 2018

Related U.S. Application Data (60) Provisional application No. 62/365,552, filed on Jul. 22, 2016.

(51) Int. Cl.
*A61B 10/00* (2006.01)
*A61B 10/02* (2006.01)
*B01L 3/00* (2006.01)

(52) U.S. Cl.
CPC .......... *A61B 10/0045* (2013.01); *A61B 10/02* (2013.01); *B01L 3/502* (2013.01); *B01L 3/505* (2013.01); *B01L 3/50273* (2013.01)

(58) Field of Classification Search
CPC ..... A61B 10/0045; A61B 10/02; B01L 3/502; B01L 3/50273; B01L 3/505
See application file for complete search history.

(56) References Cited

U.S. PATENT DOCUMENTS

| 4,615,341 A | * | 10/1986 | Marzolf | A61B 5/15003 600/578 |
| 5,879,635 A | * | 3/1999 | Nason | B01L 3/0272 206/209 |
| 2002/0136665 A1 | * | 9/2002 | Hayton | A61B 10/0051 422/400 |
| 2003/0209653 A1 | * | 11/2003 | Feldsine | G01N 21/76 250/214 R |
| 2013/0181010 A1 | * | 7/2013 | Ouyang | H01J 49/16 222/209 |

* cited by examiner

*Primary Examiner* — Brian R Gordon
*Assistant Examiner* — Dwan A Gerido
(74) *Attorney, Agent, or Firm* — Finnegan, Henderson, Farabow, Garrett & Dunner, LLP (57) ABSTRACT

A collection device is disclosed having a tubular housing detachably receiving a valved bulb reservoir at a first end thereof, the housing having a second end for dispensing fluids. The valved bulb reservoir has a sample capillary tube attached at one end thereof. The bore of the capillary is fluidically coupled to the valved bulb reservoir. The capillary is removed from the tubular housing to collect a sample in its bore, and is then replaced into the tubular housing. The contents of the valved tubular reservoir, which can be a buffer solution, a reagent, or other analytic fluid, or a gas, are then passed through the capillary bore to expel the sample and mix therewith in the housing. The sample product can then be dispensed from the tubular housing.

10 Claims, 7 Drawing Sheets

SELF-CONTAINED SAMPLING DEVICE FOR PROCESSING WHOLE BLOOD

PRIORITY CLAIM

This application claims priority from U.S. Provisional Patent Application No. 62/365,552 filed on Jul. 22, 2016, which is hereby incorporated by reference in its entirety in the present application.

BACKGROUND

The present disclosure generally relates to devices for biological or medical sampling of fluids. More particularly, and without limitation, the present disclosure relates to a self-contained diagnostic sampling device for processing whole blood and dispensing the processed whole blood.

The prior art includes a device described in U.S. Pat. No. 5,869,003 that includes a specimen swab and a squeeze bulb that retains buffer until a snap-valve is cracked. Other known devices, such as those offered by Medical Packaging, Inc. of Camarillo, Calif. include collection tubes packed with fibrous filter material to draw blood before cracking the snap-valve. Using a filter material for wicking blood provides several disadvantages. Filter materials draw blood much more slowly than using a capillary directly. Further, when a filter material is used for wicking blood, the volume of blood that can be drawn is limited to the saturation volume of blood that the filter can hold. Still further, pressing a filter material into a small tube during manufacturing is cumbersome and difficult. In addition, the filtration provided by a blood-wicking filter is an otherwise unnecessary component for certain whole-blood analyses, rendering a filter an unnecessary material cost.

In view of the above and other factors, known collection devices suffer from numerous drawbacks. These drawbacks are especially acute in situations where rapid processing of blood or other samples is needed.

SUMMARY

The disclosed embodiments include self-contained consumables for drawing fluids, such as whole blood from a finger stick, for further processing or analysis, such as direct use in a nucleic acid amplification tests or lateral flow assays. According to exemplary embodiments, a sample collection device includes a tubular housing having a first end and a second end; a valved bulb reservoir detachably fitted to the first end of the tubular housing; and a capillary having a longitudinal bore connected by a first end and a second end, the capillary attached and fluidically coupled to the valved bulb reservoir at the first end, and the second end configured for receiving sample into the longitudinal bore.

According to another aspect of the present disclosure, a sample collection device includes a capillary adapter for fluidically coupling the capillary to the valved bulb reservoir. In a still further aspect of the present disclosure, a capillary adapter can be configured for venting a capillary bore.

According to other aspects of the disclosure, a method is described for collecting a sample, including providing a collection device comprising a tubular housing having a first end and a second end, a valved bulb reservoir detachably fitted to the first end of the tubular housing, a capillary having a longitudinal bore connected by a first end and a second end, the capillary attached and fluidically coupled to the valved bulb reservoir at the first end, and the second end configured for receiving sample into the longitudinal bore; and removing the valved bulb reservoir and capillary from the tubular housing; and applying the capillary to a fluid to draw a sample into the capillary bore.

Embodiments according to the present disclosure solve many problems in the prior art. Exemplary embodiments discussed herein provide exceptional ease of use in a clinical or field setting. A minimally trained individual can draw blood from a finger stick. Exemplary embodiments of the present disclosure also provide for more rapid sample acquisition than possible in the prior art. Exemplary embodiments of the present disclosure can achieve whole blood draw from a subject's finger stick in as little as one second, which is not possible using a capillary filter or swab.

Advantageously, embodiments according to the disclosure facilitate the ease and speed of sample acquisition, contributing to the comfort of the subject in the case of a blood draw, for example, the ability to collect a sample at the point-of-care, as well as the training level required of the health care worker taking the sample.

According to some exemplary embodiments, sample collection devices are employed for collection of whole blood for use in nucleic acid amplification tests or lateral flow assays without the need for a venous puncture.

According to one illustrative embodiment of the disclosure, a capillary is employed for directly drawing blood. Prior art devices use collection tubes with larger diameters than capillaries. As a result, prior art devices are not capable of capillary action (i.e. pulling up a fluid into the tube) unless a filter is placed in the lumen of the tube to supply the capillary effect. Illustrative embodiments of the disclosure do not use a filter material for drawing blood.

According to an exemplary embodiment, a capillary tube is provided with vent holes in at least one of several possible locations in the collection device. Exemplary embodiments do not require forming a vent hole through a side of a capillary, which as a small tube requires very tight tolerances and a difficult manufacturing step.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

DETAILED DESCRIPTION

The disclosed embodiments relate to devices for rapid collection of fluid samples, such as whole blood from a subject or patient. As a result, samples can be collected at the point-of-care for processing or analysis by personnel having very little training.

When collecting blood from a patient for use in a nucleic acid amplification reaction or a lateral flow assay, the blood must be taken from the patient and transferred into a sample reservoir. The ease and speed with which a sample can be taken from a patient influences the comfort of the patient, the ability to apply the sample collection method at the point-of-care, and the training level required of the health care worker taking the sample. According to one aspect of the disclosure; rapid and simple collection of whole blood and use in a nucleic acid amplification test or a lateral flow assay is provided without the need for a venous puncture. Additionally, according to another aspect of the disclosure, collection of blood and transfer to another reservoir is avoided, bypassing the need for the use of anticlotting agents in the sample that could otherwise be indicated.

Figure 1:
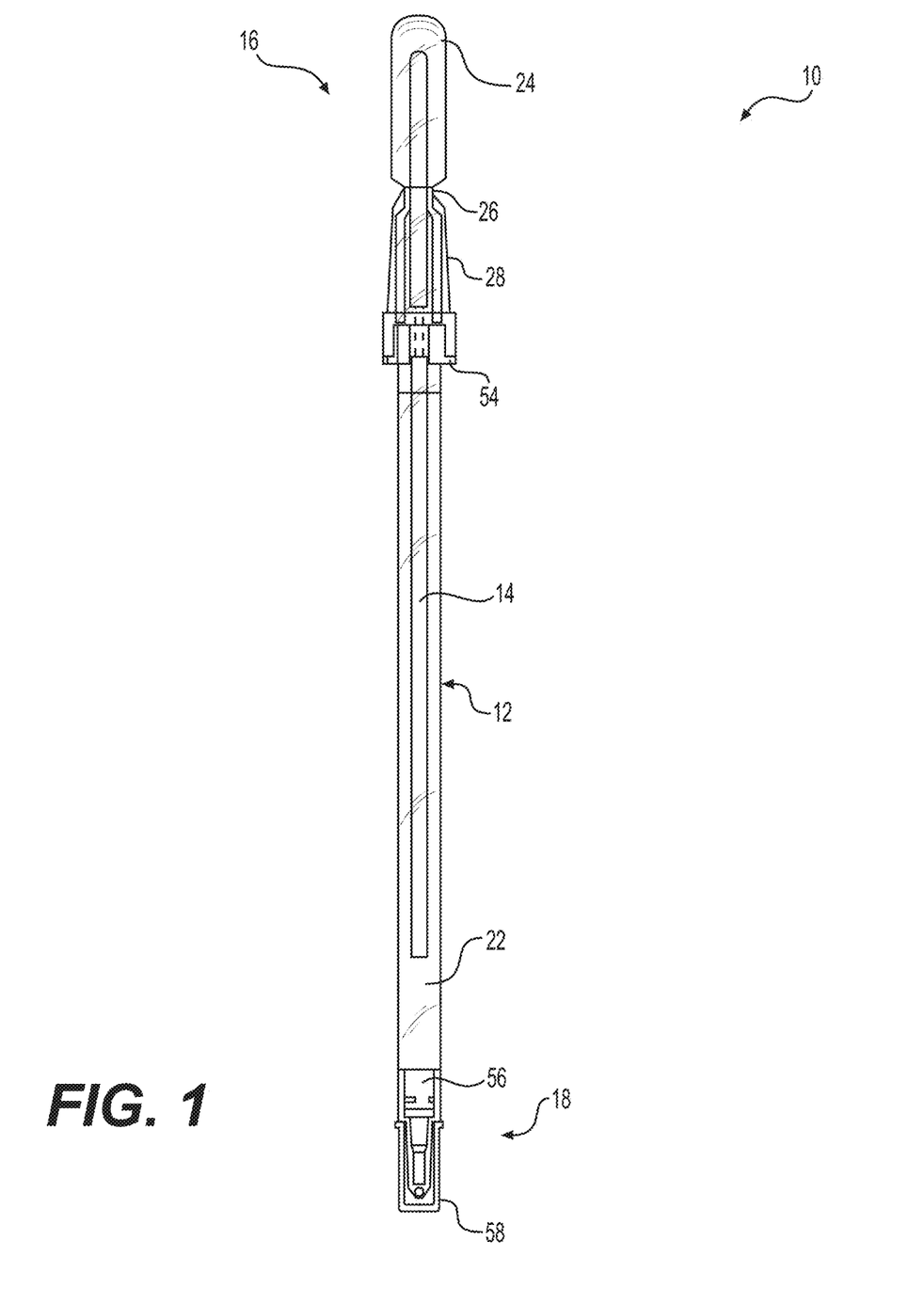
FIG. 1 is a side elevational view according to one exemplary embodiment of the disclosure.
Figure 3:
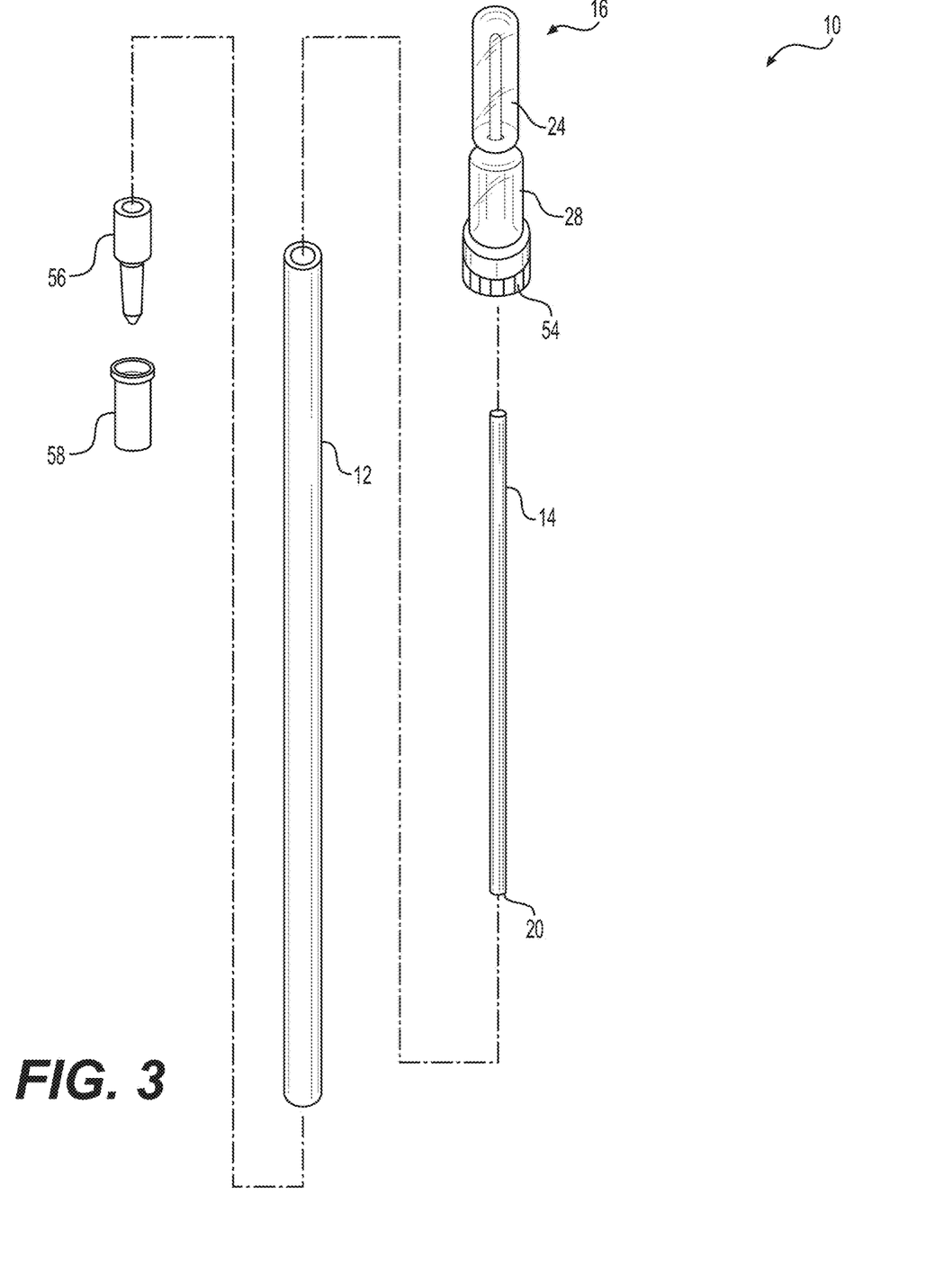
FIG. 3 is an exploded perspective view of an exemplary embodiment of the disclosure.

As shown in FIGS. 1 and 3 an illustrative embodiment of a sample collection device 10 is shown. The sample collection device 10 may have an elongated tubular housing 12 into which a capillary 14 or the like may be received. A valved reservoir 16, which is attached to the capillary 14, is removably mounted at one end of tubular housing 12. In an illustrative embodiment, valved bulb reservoir 16 may contain one or more fluids or reagents used in fluid analysis, which can be dispensed and mixed with a sample collected in capillary 14. In an alternative embodiment, the valved bulb reservoir 16 contains a gas, such as air. An end cap assembly 18 may be mounted at an opposite end of tubular housing 12 and may include a dispensing spout 56 and a removable cover or cap 58. Dispensing spout 56 can optionally include one or more filters, for example for removing erythrocytes from a sample. Further, such filter(s) can be selected so as to avoid lysing of erythrocytes during dispensing from the spout. A sample is obtained by a user by placing capillary tip 20 proximate to a fluid to be analyzed to draw it into the capillary, as described in greater detail below.

In an illustrative embodiment, sample collection device 10 provides a relatively simple, compact and cost-efficient device for collecting and substantially immediate on-site testing of biological specimens such as tissue, cells, body fluid, and the like obtained from a patient, or from another target source such as food products, biological cultures, etc. Sample collection device 10 advantageously permits quick and easy specimen collection with capillary 14 removed from tubular housing 12, followed by dispensation of analytical fluid, for example buffer solution, from valved bulb reservoir 16 through the capillary, to expel the sample and the analytical fluid into the tubular housing 12 for mixing. Thereafter, the sample mixed with any analytic fluid can be dispensed from tubular housing 12, for example via spout 56 in an illustrative embodiment, for downstream analysis.

In an alternative embodiment, valved bulb reservoir 16 can contain a plurality of analytic fluids, for example reagents, which can be sequentially mixed prior to contact with a sample in capillary 14, as discussed in greater detail below. Advantageously, sample collection device 10 permits sample collection, mixing and dispensing by untrained users within a self-contained and disposable device.

According to a further aspect of the disclosure, sample collection device 10 may be elongated and dimensioned for convenient manual handling during use. Capillary 14 as shown terminates above end cap assembly 18 in order to form a chamber 22 for mixing sample obtained in capillary 14 with any analytic fluid from valved bulb reservoir 16. Of course, valved bulb reservoir could contain only air, or other gas, allowing sample to be ejected into chamber 22 without analytic fluid.

Capillary 14 is dimensioned for convenient placement, following collection of a sample via capillary tip 20, into tubular housing 12. Capillary 14 can be formed of glass or polymeric material, such as polycarbonate, as can tubular housing 12. In an illustrative embodiment, the hollow interior of tubular housing 12 defines chamber 22 at a portion thereof. A lower or distal end of chamber 22 is closed by end cap assembly 18 mounted on tubular housing 12, and an upper or proximal end of tubular housing 12 is closed by valved bulb reservoir 16 removably mounted onto tubular housing 12 in a manner permitting capillary 14 to be placed therein. As shown, for best test results, capillary 14 is placed into the chamber 22 with capillary tip 20 positioned generally at the proximal end of tubular housing 12 adjacent to end cap assembly 18.

According to a further aspect of the present disclosure, end cap assembly 18 includes spout 56 for controlled or regulated delivery of sample, which can be mixed with one or more analytic fluid or reagent in liquid form added to the chamber 22 by manipulation of valved bulb reservoir 16. Upon contacting capillary tip 20 to the sample, the sample flows upwardly by capillary action, and is held in capillary 14 thereby.

Figure 2A:
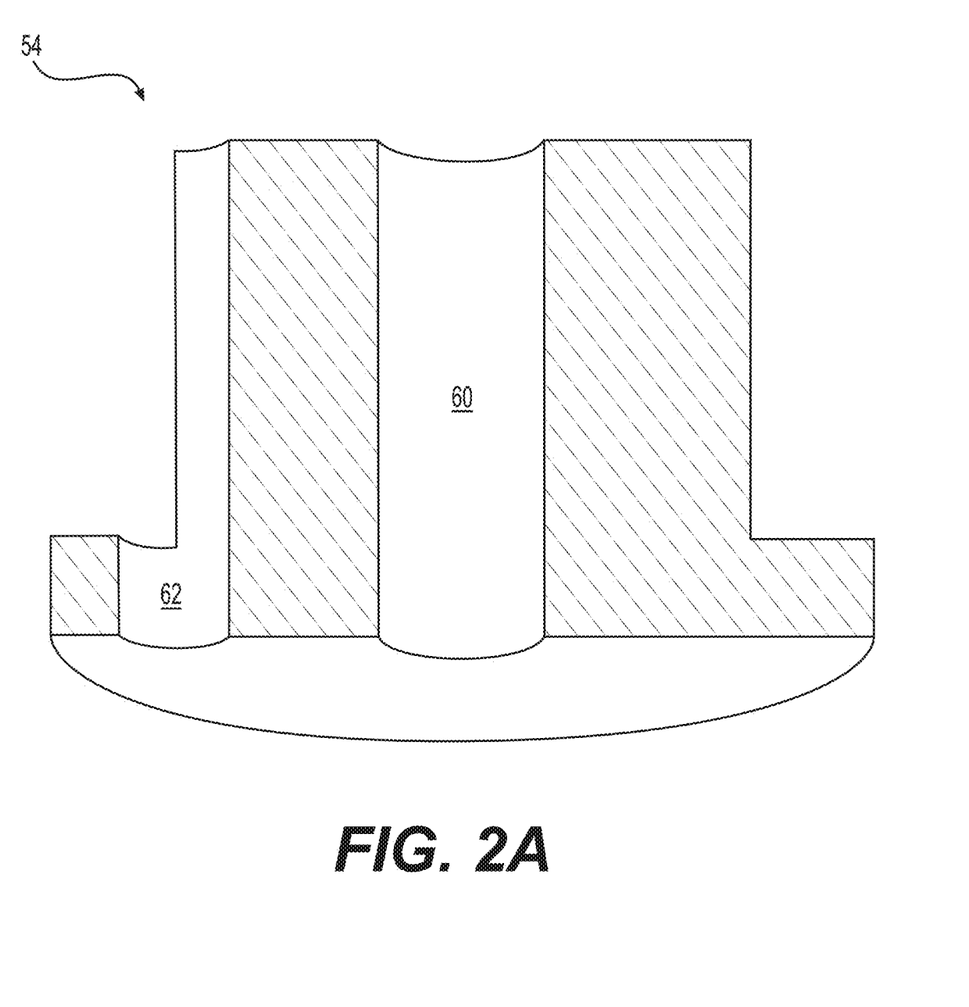
FIG. 2A and FIG. 2B are cross-sectional views of illustrative embodiments of a capillary adapter according to the disclosure.

As shown in FIG. 2A, a capillary adapter 54 is shown in cross-sectional detail. Capillary adapter 54 has a capillary bore 60 for sealingly receiving and retaining capillary 14 to valved bulb reservoir 16, so that capillary tip 20 can be conveniently maneuvered into position to collect sample by a user holding the valved bulb reservoir 16. In an illustrative embodiment of capillary adapter 54, a vent 62 is provided to permit air displaced by sample in the bore of capillary 14 to escape. Vent 62 can be placed anywhere to provide a path for displaced air from the bore of capillary 14 to escape, and needn't be placed as depicted. Advantageously, venting can be achieved by means other than forming a vent hole in the wall of the capillary tube itself, which is an exacting and costly process.

Figure 2B:
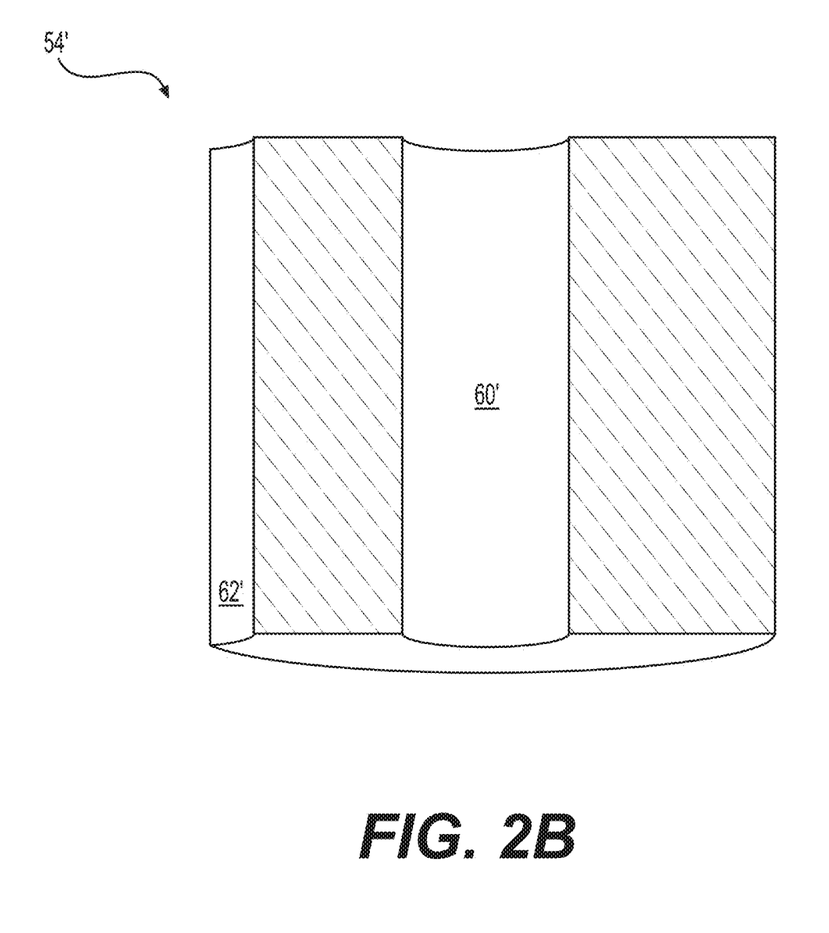

As shown in FIG. 2B, a capillary adapter 54' is shown in cross-sectional detail. Capillary adapter 54' has a capillary bore 60' for sealingly receiving and retaining capillary 14 to valved bulb reservoir 16, so that capillary tip 20 can be conveniently maneuvered into position to collect sample by a user holding the valved bulb reservoir 16. In an illustrative embodiment of capillary adapter 54', a vent 62' is provided to permit air displaced by sample in the bore of capillary 14 to escape. Vent 62' can be placed anywhere to provide a path for displaced air from the bore of capillary 14 to escape, and needn't be placed as depicted. Advantageously, venting can be achieved by means other than forming a vent hole in the wall of the capillary tube itself, which is an exacting and costly process.

Figure 4:
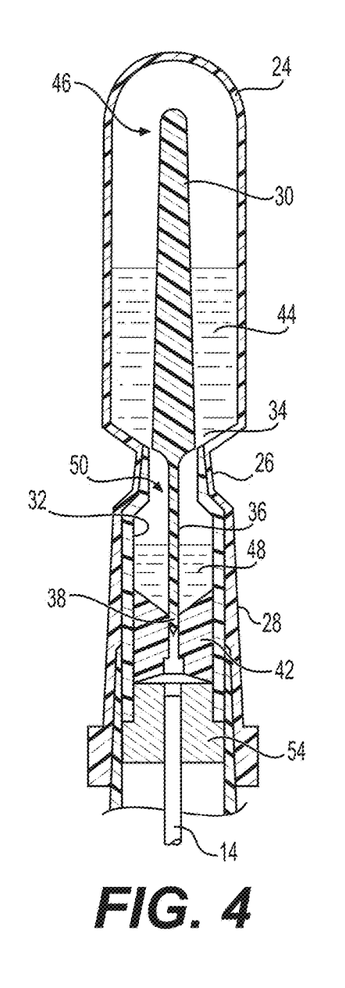
FIG. 4 is a cross-section view of an upper portion of an illustrative embodiment of the disclosure.
Figure 5:
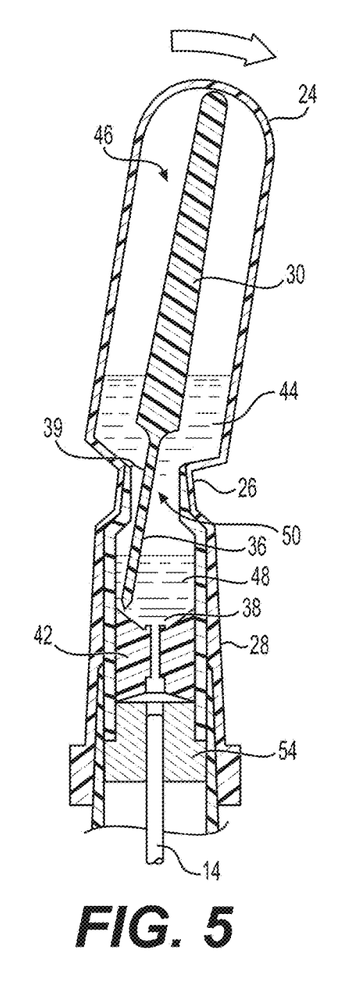
FIG. 5 is a cross-section view of an upper portion of an illustrative embodiment of the disclosure showing movement of a toggle to break a frangible seal.
Figure 6:
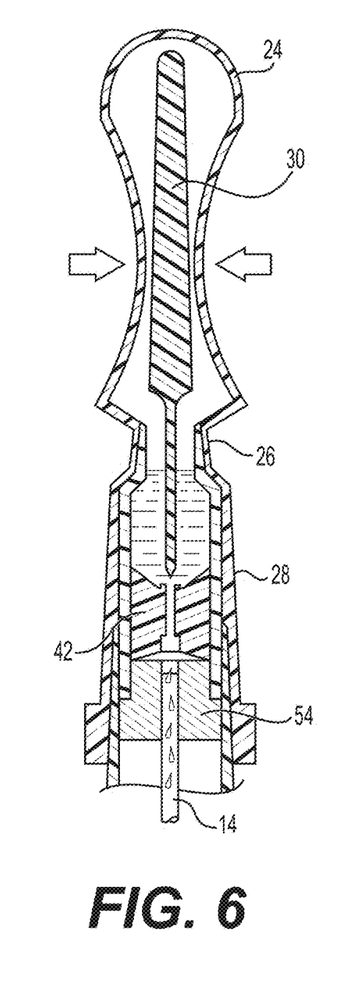
FIG. 6 is a cross-section view of an upper portion of an illustrative embodiment of the disclosure showing squeezing of a bulb reservoir.

An illustrative embodiment of valved bulb reservoir 16 is shown in greater detail in one preferred form in FIGS. 4-6. As shown, valved bulb reservoir 16 comprises bulb 24 joined integrally by a narrowed portion 26 to a lower portion 28. Bulb 24 may be formed of transparent material to permit viewing its interior. In an exemplary embodiment, a movable device such as toggle 30 can be provided, as described below. In an illustrative embodiment, lining member 32 can be fitted onto lower portion 28. Lining member 32 may have an upper end which passes through narrowed portion 28, which may be joined integrally by a frangible seal 34 to toggle 30, which may project upwardly into the interior of bulb 24. Other shapes are of course possible. In an illustrative embodiment, a toggle stem 36 may be provided as an extension of toggle 30 to engage and sealingly close an outlet 38 formed in a plug member 42 fitted into lining member 32.

In exemplary embodiments, valved bulb reservoir 16 may contain one or more analytical fluids, chemical reagents, etc., as shown in liquid form in FIGS. 4-6. A first fluid 44 may be placed into a first space 46 within the interior volume of bulb 24, followed by fitting toggle 30 so that the upper end of lining member 32 seals through narrowed portion 26, in cooperative relation with frangible seal 34 and, optionally, toggle stem 36. A second fluid 48 may then be placed into the interior of lining member 32 followed by fitting plug member 42 in a position with toggle stem 36 closing outlet 38.

When it is desired to process a sample, valved bulb reservoir 16 is placed on the upper or proximal end of tubular housing 12 to enclose capillary 14 with a sample in its bore within the chamber 22, as shown in FIG. 1. In an illustrative embodiment having two analytic fluids, valved bulb reservoir 16 is then manipulated by a user to intermix fluids 44 and 48 by initially bending or deforming bulb 24 as shown by the arrow of FIG. 5 to cause displacement of toggle 30 to rupture frangible seal 34. This action breaks the seal between first space 46 and second space 50, to enable the two reagents to flow together and mix. Of course, if there is only one analytic fluid, these features would not be necessary. Further displacement of bulb 24 will retract toggle stem 36 from outlet 38, as shown in FIG. 5. Squeezing bulb 24 may then express the analytic fluid(s) through outlet 38 into capillary 14. The fluids expressed through the bore of capillary 14, with sample collection device 10 held in an essentially upright orientation, will urge the sample and any analytic fluids into chamber 22, thereby mixing them. If there are no analytic fluids, air from the bulb can expel sample from the bore of capillary 14 in like manner.

Some fluid may be retained in bulb 24 after expressing the analytic fluid(s) through outlet 38 into capillary 14. As a result, the sample to analytic fluid ratio may not be precise. Some applications may require precise sample to analytic fluid ratios. In an illustrative embodiment sample collection device 10 may be configured into two assemblies to provide a precise ratio of sample to buffer. A housing assembly consisting of 12, 56, and 58 may be delivered with buffer stored in housing 12. The housing assembly may be sealed on one end by cap 58, and on the other end by a heat seal or a sealing plug (not shown). A capillary assembly consisting of 24, 28, 54, and 14 may be delivered with air or other gas in bulb 24 (rather than liquid buffer). Upon contacting capillary tip 20 to the sample, the sample flows upwardly by capillary action, and is held in capillary 14 thereby. Any heat seal or sealing plug may then be removed from the housing assembly, and the capillary assembly placed into the housing assembly. Displacement of toggle 30 ruptures frangible seal 34. Squeezing bulb 24 then expresses the air through capillary 14, mixing the sample in capillary 14 with the buffer predisposed in housing 12, resulting in a precise ratio of sample to buffer.

Figure 7:
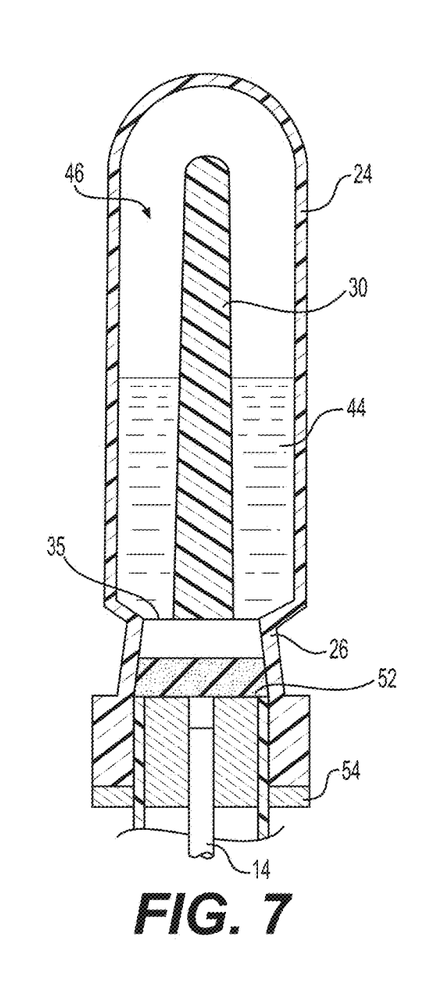
FIG. 7 is a cross-section view of an upper portion of a further illustrative embodiment of the disclosure.
Figure 8:
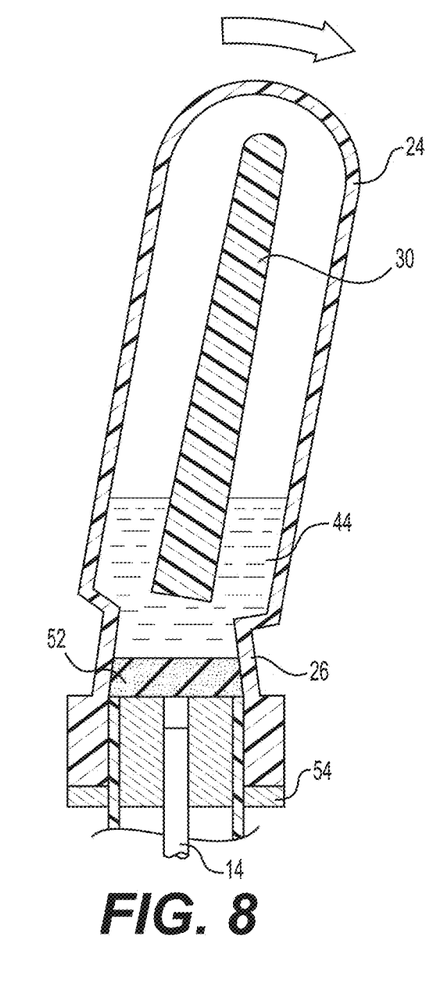
FIG. 8 is a cross-section view of an upper portion of an illustrative embodiment of the disclosure showing movement of a toggle to break a frangible seal.
Figure 9:
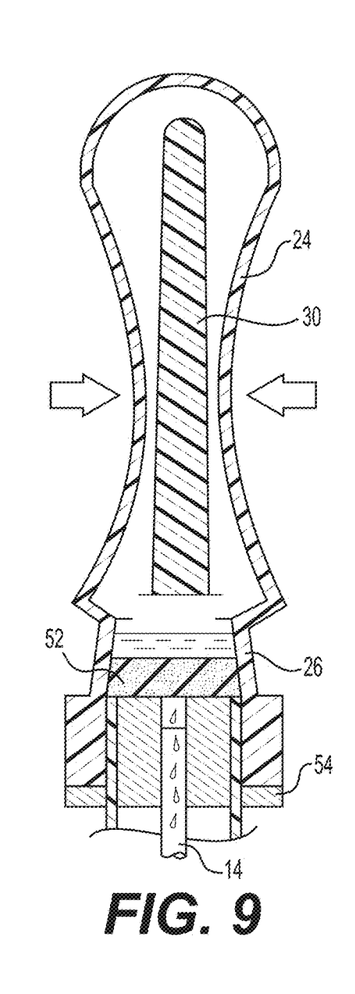
FIG. 9 is a cross-section view of an upper portion of an illustrative embodiment of the disclosure showing squeezing of a bulb reservoir.
Figure 10:
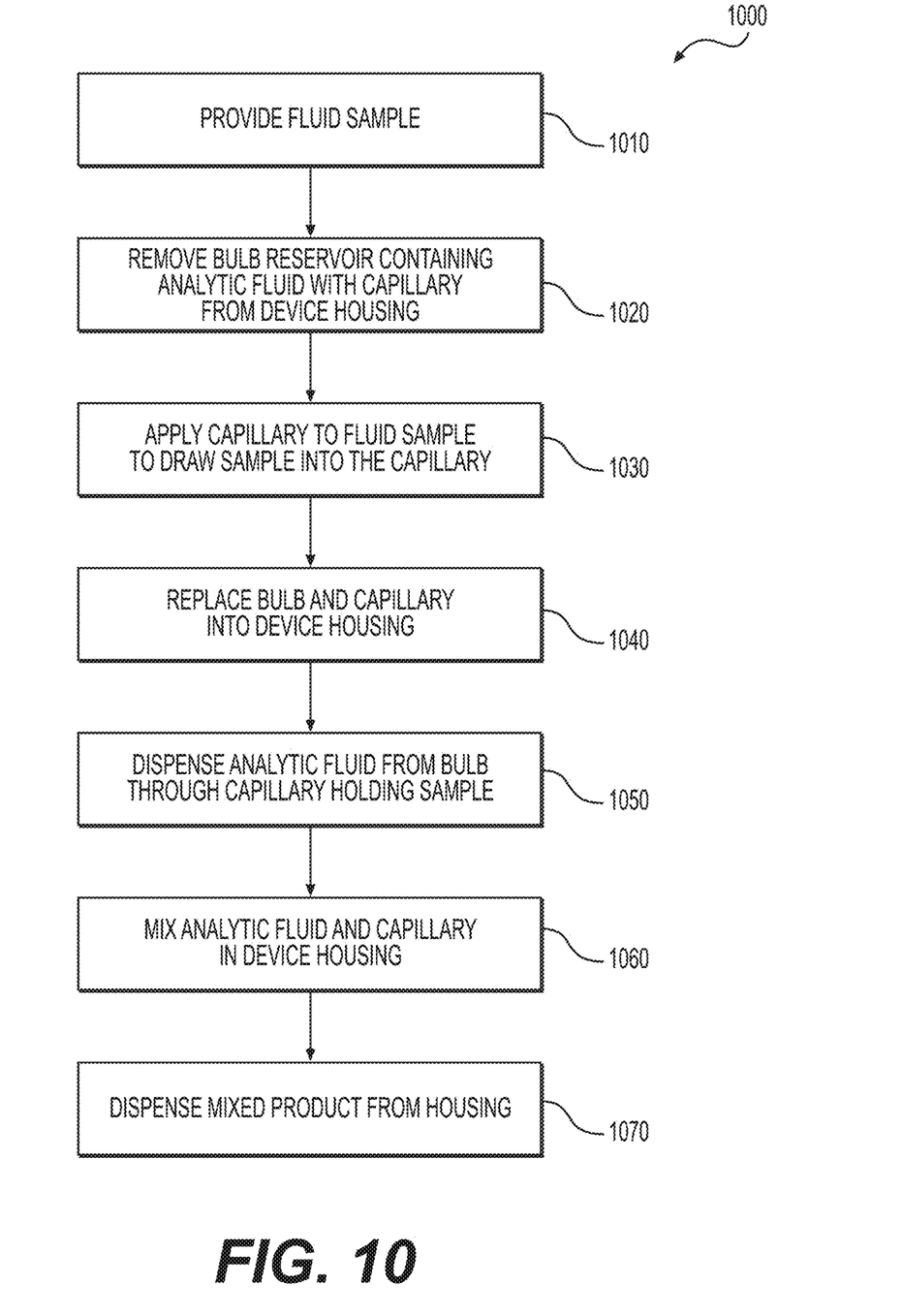
FIG. 10 is a flowchart depicting a method of using exemplary devices of the disclosure.

FIGS. 7-9 show an additional illustrative embodiment of valved bulb reservoir 16, wherein a second processing element 52 is provided. Element 52 can be one or more filters, which can include a reagent in solid form, for example. First space 46 is normally closed by frangible seal 35. Element 52 is installed within a neck region of the bulb. FIG. 8 depicts displacement of bulb 24 to bend the toggle 30 sufficiently to sever frangible seal 34 and thereby release the fluid 44 for flow to element 52. FIG. 10 illustrates squeezing of bulb 24 to deliver the fluid 44 through element 52, with concomitant mixing with any reagent carried by element 52, for delivery through the bore of capillary 14 to chamber 22, as previously described. Of course, element 52 may be omitted in the case where a single analytic fluid is used.

End cap assembly 18 as shown in the illustrative embodiment of FIGS. 1 and 3 may include a spout 56 fitted to the end of tubular member 12. The spout can be of any size or configuration based on the use of the device. For instance, spout 56 can be a dropper tip, a fast-flow nozzle, a spray tip, etc. In an illustrative embodiment, spout 56 can include a filter, for example for filtering out red blood cells in a whole blood assay. Cap 58 can include features for sealing and retaining the cap on device 10, as generally known in the art. Cap 58 can also include a desiccant.

As one example of use of the sample collection device 10, the device may be employed as depicted by illustrative method 1000 depicted in the flowchart of FIG. 10. A fluid sample is made available at step 1010. The sample could be whole blood, which is made available on a fingertip using a lancet, for example. At step 1020, a bulb reservoir with a capillary is removed from the device housing, and at step 1030, the capillary is applied to the fluid sample to draw sample into the capillary. At step 1040, the bulb and capillary are replaced into the device housing. At step 1050, analytical fluid contained in the bulb is dispensed through the capillary, expelling the sample into the housing. At step 1060, the analytic fluid and the sample are mixed together, and at step 1070 after an appropriate period of time according to a procedural protocol, the mixed product is dispensed from the device housing.

Devices and methods according to the present disclosure can additionally be used to analyze blood, serum, urine or plasma from a test tube using the device. While some exemplary embodiments use a capillary to draw blood from a finger stick, it is also envisioned to integrate a lancet and/or needle directly into the device, so that the puncture for the blood draw can be integrated into the device. Further, although illustrative embodiments of the disclosure use a valved bulb reservoir, other types of valves and reservoirs are possible, such as check valve, an umbrella valve, or an ePTFE vent. It is only important that the valve retain analytic fluid until the user is ready to release it into the sample, and that the valve prevents fluid loss or contamination during storage.

EXAMPLES

A polymerase chain reaction (PCR) testing for Chromosome 19 was run to demonstrate the utility of devices according to the present disclosure in processing whole blood. In one sample, a device substantially as depicted in FIGS. 1 and 3 was used to process whole blood. Another sample of whole blood was used with the same buffering system as before, but without the device according to present disclosure. A further test was run where whole blood was buffered with water. A further test was run where whole blood was added directly to the nucleic acid amplification reaction. The sample processed using the device according to the present disclosure returned a CT Value (FAM) of 35.2. The other approaches tested negative, because whole blood is inhibitory to nucleic acid amplification reactions unless it is processed properly (i.e., removing erythrocytes, using an appropriate buffer, etc.). Whole blood directly in PCR causes inhibition for at least two reasons: iron in heme is inhibitory; and the coloration of erythrocytes can interfere with optical measurements.

A lateral flow assay for Abrin was run to demonstrate the utility of devices according to the present disclosure in processing whole blood. A test with a single line is a negative test for Abrin (control line only). A test with two lines is a positive for Abrin (control line and test line). Whole blood is expected to test negative for Abrin.

In a first test, a device substantially as depicted in FIGS. 1 and 3 was used to process whole blood. In a second test, whole blood was used with the same buffering system as in the first test, but without using a device according to the present disclosure. In a third test, whole blood was added directly to the lateral flow assay. The first test resulted in a clear background and a control line on the lateral flow assay. The second test showed a streaky background and a control line. Streaky backgrounds are undesirable in lateral flow assays because they increase the chance of false positives. The third test failed to wick completely, and no control line was apparent, rendering the test invalid.

The improved sample collection device of the present disclosure provides a simple and easy-to-use apparatus in a substantially self-contained compact form factor. Personnel exposure to the collected sample and its processing is substantially limited. With the sample introduced into the collection device, a test procedure can be performed quickly and easily. The delivery of the processed sample to downstream analysis quickly. The dimensions of the test unit provide a compact and ergonomic package. At the conclusion of a test, the test unit can be economically and easily discarded in accordance with normal disposal practices.

A variety of further modifications and improvements in and to the sample collection device of the present invention will be apparent to those skilled in the art. Accordingly, no limitation on the invention is intended by way of the foregoing description and accompanying drawings, except as set forth in the appended claims. The foregoing description has been presented for purposes of illustration. It is not exhaustive and is not limited to precise forms or embodiments disclosed. Modifications and adaptations of the embodiments will be apparent from consideration of the specification and practice of the disclosed embodiments. In addition, while certain components and arrangements have been described, other components and arrangements may be implemented, as will be appreciated from this disclosure.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed:

1. A sample collection device comprising:
   a tubular housing having a first end and a second end;
   a valved bulb reservoir detachably fitted to the first end of the tubular housing;
   a capillary having a longitudinal bore, a first end, and a second end, the capillary attached and fluidically coupled to the valved bulb reservoir at the first end, and the second end comprising a capillary tip configured to directly receive a liquid sample into the longitudinal bore by capillary action; and
   a capillary adapter for fluidically coupling the capillary to the valved bulb reservoir,
   wherein the capillary adapter is attached to the valved bulb reservoir and comprises a bore configured to receive the first end of the capillary, and
   wherein the capillary adapter comprises a vent hole for allowing air in the longitudinal bore to be displaced out of the longitudinal bore by the liquid sample.

2. The sample collection device of claim 1, further comprising an end cap assembly at the second end of the tubular housing.

3. The sample collection device of claim 1, wherein the capillary is formed of a glass or polymeric continuous tube.

4. The sample collection device of claim 1, further comprising a frangible seal in the valved bulb reservoir for fluidically isolating the valved bulb reservoir from the capillary bore.

5. The sample collection device of claim 2, further comprising a spout.

6. The sample collection device of claim 2, further comprising one or more filters.

7. The sample collection device of claim 2, further comprising a removable cap covering the second end of the tubular housing.

8. The sample collection device of claim 4, wherein the frangible seal is rupturable by manipulation.

9. The sample collection device of claim 8, further comprising a toggle operatively coupled to the frangible seal, wherein manipulation of the toggle ruptures the frangible seal.

10. The sample collection device of claim 1, wherein the bore of the capillary adapter is configured to sealingly receive the first end of the capillary and attach the capillary to the valved bulb reservoir.

* * * * *